US006391609B1

(12) United States Patent
Goldford

(10) Patent No.: US 6,391,609 B1
(45) Date of Patent: May 21, 2002

(54) THROMBOPLASTIN REAGENTS AND METHODS FOR PREPARING AND USING SUCH REAGENTS

(75) Inventor: Marc D. Goldford, Ballwin, MO (US)

(73) Assignee: Sigma-Aldrich Co., Highland, IL (US)

( * ) Notice: Subject to any disclaimer, the term of this patent is extended or adjusted under 35 U.S.C. 154(b) by 0 days.

(21) Appl. No.: 09/413,683

(22) Filed: Oct. 7, 1999

Related U.S. Application Data
(60) Provisional application No. 60/103,417, filed on Oct. 7, 1998.

(51) Int. Cl.⁷ ............................. C12N 9/48; A61K 35/14

(52) U.S. Cl. ........................................ 435/212; 530/381
(58) Field of Search ............................ 230/381; 435/212

(56) References Cited

U.S. PATENT DOCUMENTS

| | | | |
|---|---|---|---|
| 2,847,350 A | 8/1958 | Singher et al. | 167/74 |
| 3,522,148 A | 7/1970 | Adam et al. | 195/99 |
| 3,862,314 A | 1/1975 | Zwisler et al. | 424/105 |
| 3,980,432 A | 9/1976 | Trobisch et al. | 23/230 B |
| 3,983,004 A | 9/1976 | Trobisch et al. | 195/99 |
| 4,361,510 A | 11/1982 | Mitra | 260/112 B |
| 4,416,812 A | 11/1983 | Becker et al. | 260/112 R |
| 4,495,175 A | 1/1985 | Chavin et al. | 424/101 |
| 4,755,461 A | 7/1988 | Lawson et al. | 435/13 |
| 5,017,556 A | 5/1991 | O'Brien et al. | 514/2 |
| 5,270,451 A | 12/1993 | Hawkins et al. | 530/381 |
| 5,358,853 A | 10/1994 | Butler et al. | 435/13 |
| 5,391,380 A | 2/1995 | Barrow et al. | 424/570 |
| 5,426,031 A | 6/1995 | Hawkins et al. | 435/13 |
| 5,508,170 A | 4/1996 | Butler et al. | 435/13 |

FOREIGN PATENT DOCUMENTS

| | | | |
|---|---|---|---|
| CA | 658579 | 2/1963 | 167/58.5 |

OTHER PUBLICATIONS

Magerovskii et al., "Partial purification of tissue thromboplastin by means of gel filtration and reproduction of the syndrome of generalized decompensated throminogenesis using the preparation obtained", Vopr. Med. Khim. 34 (3):34–9 (1988).*
Scopes, Protein Purification, second edition, Springer–Verlag, "Ultrafiltration" pp. 218–220 (1987).*
Pitlick et al. "Purification and Characterization of Tissue Factor Apoprotein," Methods of Enzymology, vol. 45, pp. 37–48 (1976).
Williams et al. "Improved Procedure for the Purification of Thromboplastin Apoprotein from Porcine Brain," Biochemical Society Transactions, vol. 16, No. 4, pp. 570–571 (1988).
Adcock et al. "Effect of 3.2% vs 3.*% Sodium Citrate Concentration on Routine Coagulation Testing" Coagulation and Transfusion Medicine, vol. 107, No. 1, pp. 105–110, 1997.
Bach et al. "Purification and Characterization of Bovine Tissue Factor" The Journal of Biological Chemistry, vol. 256, No. 16, pp. 8324–8331, 1981.
Biggs et al. "Human Blood Coagulation and Its Disorders, Second Edition" pp. 392–395, 1957.
Bjørklid et al. "Purification and Some Properties of the Protein Component of Tissue Thromboplastin from Human Brain" Biochem. J. vol. 165, pp. 89–96, 1977.
Bjöquist et al. "Determination of the Kinetic Constants of Tissue Factor/Factor VII/Factor VIIA and Antithrombin/ Heparin Using Surface Plasmon Resonance" Thrombosis Research, vol. 85, No. 3, pp. 225–236, 1997.
Bradlow et al. "A Human Brain Thromboplastin Standard for Distribution in South Africa" SA Medical Journal, Nov. 10, 1976, pp. 1989–1992.
Chantarangkul et al. "Influence of Citrate Concentration on the International Sensitivity Index (ISI) of Five Thromboplastins" Thromb. Haemostasis, vol. 73, No. 6, Abstract No. 1287, 1995.
Guha et al. "Affinity Purification of Human Tissue Factor: Interaction of Factor VII and Tissue Factor in Detergent Micelles" Proc. Natl. Acad. Sci. USA, vol. 83, pp. 299–302, 1986.
Howell et al. "The Role of Lipoproteins in the Production of Hypercoagulability: A New Concept" British Journal of Experimental Pathology, vol. XLV, No. 6, pp. 618–626, 1964.
O'Brien et al. "Structural Requirements for the Interaction Between Tissue Factor and Factor VII: Characterization of Chymotrypsin–derived Tissue Factor Polypeptides" Biochem. J., Vol. 292, pp. 7–12, 1993.
Poller "Standardization of Anticoagulant Treatment: The Manchester Regional Thromboplastin Scheme" British Medical Journal, Aug. 29, 1964, pp. 565–566.
Quick "Thromboplastin as a Reagent" Am. J. Med. Sci., vol. 190, No. 501, pp. 585–592, 1935.

(List continued on next page.)

Primary Examiner—Sandra E. Saucier
(74) Attorney, Agent, or Firm—Senniger, Powers, Leavitt & Roedel

(57) ABSTRACT

Disclosed are mammalian thromboplastin reagents and methods for preparing such reagents. The thromboplastin reagents are suitable for use in prothrombin-time (PT) assays, and offer improved sensitivities with acceptable PT-normal times. Contaminating proteins—particularly plasma clotting factors—are separated from a thromboplastin solution by a membrane permeation protocol, in which the thromboplastin solution is exposed to a semipermeable membrane and clotting factors are allowed to pass from the thromboplastin solution through the membrane, while Tissue Factor is retained in the thromboplastin solution. In a preferred method, one or more contaminating clotting factors are separated by diafiltration from a NaCl/Na₃Citrate thromboplastin extract of mammalian tissue, and the purified thromboplastin extract is combined with $Ca^{++}$ ions to form a thromboplastin reagent.

25 Claims, 5 Drawing Sheets

OTHER PUBLICATIONS

Spurling et al. "The Influence of Residual Factor VII on the Sensitivity of Brain Thromboplastin" Thrombox. Haemostas., vol. 39, pp. 592–599, 1978.

Starr et al. "Prothrombin Times: An Evaluation of Four Thromboplastins and Four Machines" Pathology, vol. 12, pp. 567–574, 1980.

Stevenson et al. "The British Comparative Thromboplastin: The Relationship Between Lipid Class Composition and Procoagulant Activity" British Journal of Haematology, vol. 44, pp. 495–501, 1980.

* cited by examiner

SDS-PAGE Electrophoresis of Cleared Supernatants of Thromboplastin Extract Before and After Diafiltration.

Lane 1: Molecular Weight Standards
Lane 2: Solution Phase of Thromboplastin Extract Before Diafiltration
Lane 3: Solution Phase of Thromboplastin Extract After Diafiltration
Lane 4: Permeate from Diafiltration

THROMBOPLASTIN REAGENTS AND METHODS FOR PREPARING AND USING SUCH REAGENTS

REFERENCE TO RELATED APPLICATIONS

This application claims the benefit of U.S. Provisional Application No. 60/103,417, filed Oct. 7, 1998 and incorporated herein by reference.

BACKGROUND OF THE INVENTION

The present invention generally relates to diagnostic coagulation assays, and specifically, to thromboplastin reagents suitable for use in thromboplastin-based coagulation assays. The invention particularly relates, in preferred embodiments, to mammalian thromboplastin extracts, to methods for preparing such extracts, to thromboplastin reagents prepared therefrom, and to use of such reagents in prothrombin-time assays.

Thromboplastin reagents include active Tissue Factor which, when exposed to a plasma sample in the presence of calcium ions ($Ca^{++}$), activates the extrinsic pathway of blood coagulation. More specifically, Tissue Factor activates Factor VII in the presence of $Ca^{++}$, which in turn, activates Factor X and Factor V to initiate the formation of thrombin from prothrombin (Factor II). Thrombin is a serine endopeptidase which cleaves fibrinogen to form fibrin. Fibrin, which is soluble as a monomer, polymerizes to form a soft clot and is subsequently crosslinked to form a hard clot. The time required to form a clot upon the combination of a thromboplastin reagent and a plasma sample is a measure of the procoagulant activity of the plasma.

Diagnostic assays that employ thromboplastin reagents and are based on clotting times—typically referred to as prothrombin-time (PT) assays—have been used extensively for determining blood coagulation deficiencies associated with the extrinsic coagulation pathway. See Quick, Am. J. Med. Soc. 190:501 (1935). PT assays are employed, for example, for screening patients' plasma prior to surgery. PT assays are also employed for monitoring anticoagulant treatment with pharmaceuticals, such as coumarin (Warfarin™, Coumadin™), that affect the extrinsic coagulation pathway.

The primary performance criteria for thromboplastin reagents for use in PT assays are the coagulation time for a "normal" plasma sample, the sensitivity of the reagent and the lot-to-lot reproducibility of the reagent. The time for coagulation of a normal plasma in a PT assay, as determined by Quick, was about 12 seconds, and the 12-second "normal PT" has subsequently become an expected criteria for thromboplastin reagents in the United States. While thromboplastin reagents preferably have a PT normal time of about 12.0 seconds, times ranging from about 9.0 to about 20.0 seconds may be satisfactory under certain circumstances, and times ranging from about 9.0 to about 14.0 seconds, preferably from about 9.0 to about 13.0 seconds, are generally acceptable. The sensitivity of a thromboplastin reagent generally refers to the dynamic range in PT assay times obtained for a "normal" plasma sample as compared to a "standard abnormal" plasma sample. "Standard abnormal" plasma samples with respect to which the sensitivity of a given thromboplastin reagent is characterized include, for example, coumarinized plasma samples (e.g. plasmas treated with Coumarin™ to have an International Normalized Ratio (INR) of about 3.0), and 99%[+] Factor VII-deficient plasma samples. The clotting times associated with pooled normal plasmas (PNP), diluted PNP (e.g. 50%-diluted PNP), or the difference in such times are also useful parameters for evaluating thromboplastin reagents. Sensitivity may be quantitized in terms of ratios or as normalized ratios to allow for more meaningful comparison between assays employing different thromboplastin reagents.

The active Tissue Factor of a thromboplastin reagent is typically obtained by extracting homogenized mammalian tissue or an acetone powder thereof with a salt solution. Thromboplastin extracts—from acetone powder of rabbit brain, human brain or human placenta, for example—are combined with calcium ions ($Ca^{++}$), buffers and stabilizers to form an active thromboplastin reagent ready for use in a PT assay. However, thromboplastin reagents prepared in this manner from thromboplastin extracts are limited with respect to sensitivity. The insensitivity of thromboplastin-based assays is partially attributable to the presence of source-animal contaminating proteins in the thromboplastin solution—especially vitamin K-dependent proteins such as Factor VII, Factor IX, Factor X, Factor II, Protein C and Protein S. These contaminating proteins stem from residual endogenous blood present with the mammalian tissue from which the thromboplastin extract is prepared.

One approach for improving the sensitivity of thromboplastin reagents involves partial absorption of vitamin K-dependent clotting factors and subsequent separation thereof from the thromboplastin extract. For example, U.S. Pat. No. 5,270,451 to Hawkins et al. discloses a method for preparing a thromboplastin extract which includes treatment with $BaSO_4$ to adsorb the vitamin K-dependent clotting factors and removal with subsequent centrifugation. Detergents and chaotropic agents can be employed in combination with $BaSO_4$ to enhance the absorption and/or separation of contaminants. Other methods for improving thromboplastin reagent sensitivity have focused on optimizing the relative amounts of extract, buffer, stabilizer, preservatives, $Ca^{++}$ and other agents in the reagent composition. Such approaches, while providing improved thromboplastin reagent sensitivities, result in normal PT assay times that are unacceptably longer than the 12 seconds expected by medical practitioners.

Hence, there remains a need, particularly in the United States, for thromboplastin reagents which offer improved sensitivity, but which maintain the PT assay time for normal plasmas at the accepted value of about 12 seconds.

SUMMARY OF THE INVENTION

It is therefore an object of the present invention to prepare thromboplastin reagents that simultaneously meet each of the relevant performance criteria with respect to PT normal times, sensitivity and lot-to-lot reproducibility. It is also an object of the invention to prepare such reagents using commercially viable methods.

Briefly, therefore, the present invention is directed to the method for separating a plasma clotting factor from a thromboplastin solution comprising exposing a thromboplastin solution comprising Tissue Factor and a plasma clotting factor to a first surface of a semipermeable membrane and allowing the clotting factor to pass from the thromboplastin solution through the membrane and retaining the Tissue Factor in the thromboplastin solution.

The invention is further directed to a method for preparing a thromboplastin extract composition by extracting mammalian tissue with an extraction solution to form a thromboplastin extract, and separating a plasma clotting factor from the thromboplastin extract by membrane permeation. The invention is further directed to thromboplastin extracts prepared according to this method.

Additionally, the invention is further directed to a method for preparing a thromboplastin reagent by separating a plasma clotting factor from a thromboplastin extract by membrane permeation, and combining the thromboplastin extract with $Ca^{++}$ ions. The invention is further directed to the thromboplastin reagents prepared according to this method.

Moreover, the invention is further directed to a method for preparing a thromboplastin reagent by exposing a feed solution that comprises a thromboplastin extract to a first surface of a semipermeable membrane, the membrane having a molecular weight cut-off ranging from about 75,000 Daltons to about 2,000,000 Daltons, collecting the exposed feed solution as a retentate, and combining the retentate with $Ca^{++}$ ions. The invention is further directed to thromboplastin reagents prepared according to this method.

The present invention is further directed to a thromboplastin reagent comprising Tissue Factor extracted from mammalian tissue, and $Ca^{++}$ ions. The thromboplastin reagent having procoagulant activity as determined by a prothrombin-time assay, and having a hemoglobin concentration of less than about 2.0 mg/dl.

Also, the invention is further directed to a method for determining the clotting time of a plasma sample by preparing or obtaining a thromboplastin reagent, combining the thromboplastin reagent with the plasma sample to form an assay solution, and determining the time elapsed from formation of the assay solution to detection of clot formation in the assay solution. The invention further provides a method for determining the level of a plasma clotting factor present in a test plasma by determining the clotting times of standard plasmas having various known levels of the plasma clotting factor, preparing a standard correlation between the clotting times of the standard plasmas and the level of the plasma clotting factor in the standard plasmas, determining the clotting time of the test plasma, and correlating the determined clotting time of the test plasma to the level of the plasma clotting factor based on standard deviation.

The present invention is further directed to a method for preparing a thromboplastin extract by contacting mammalian tissue with an extraction solution comprising sodium citrate at a concentration of at least about 7 mM, whereby Tissue Factor is extracted from the tissue into the extraction solution, and separating the extraction solution from the extracted tissue.

Additionally, the present invention is further directed to a method for controlling the sensitivity of a thromboplastin reagent comprising modulating the free calcium ion content of the thromboplastin reagent with a calcium buffering agent. The present invention is further directed to a method for preparing a thromboplastin reagent by preparing a thromboplastin extract comprising a calcium buffering agent, separating a plasma clotting factor from the thromboplastin extract to form a purified thromboplastin extract, and adding calcium buffering agent to the purified thromboplastin extract.

Moreover, the present invention is further directed to a method for preparing a thromboplastin extract by extracting mammalian tissue with an extraction solution comprising a phospholipase inhibitor. The present invention also provides a method for stabilizing a thromboplastin extract by combining the thromboplastin extract with a phospholipase inhibitor. The present invention is further directed to a thromboplastin extract comprising a phospholipase inhibitor.

The thromboplastin reagents of the present invention offer substantial advantages over various prior art thromboplastin reagents by simultaneously offering, in preferred embodiments: (1) normal PT times within the acceptable range of 9.0 to 13.0 seconds and (2) acceptable sensitivities with respect to each of the characterizing criteria: a dynamic range for a coumarinized plasma having a International Normalized Ratio (INR) of about 3.0 of at least about 40 seconds; a dynamic range for a 99%+ Factor-VII-deficient plasma long enough to cover the present diagnostic and/or therapeutic ranges—preferably of at least about 40 seconds; a dynamic range for a 50% pooled-normal plasma (versus a 100% PNP) ranging from about 3 seconds to about 6 seconds; and an International Sensitivity Index (ISI) of not more than about 1.4. As such, the thromboplastin reagents can be successfully employed in PT assays for a broad range of diagnostic applications. Moreover, the methods disclosed herein for preparing thromboplastin extracts and reagents are efficient and reproducible. As such, these methods offer commercially viable means for preparing improved thromboplastin reagents.

Other features, objects and advantages of the present invention will be in part apparent to those skilled in the art and in part pointed out hereinafter. All references cited in the instant specification are incorporated by reference. Moreover, as the patent and non-patent literature relating to the subject matter disclosed and/or claimed herein is substantial, many relevant references are available to a skilled artisan that will provide further instruction with respect to such subject matter.

DETAILED DESCRIPTION OF THE INVENTION

Figure 1:
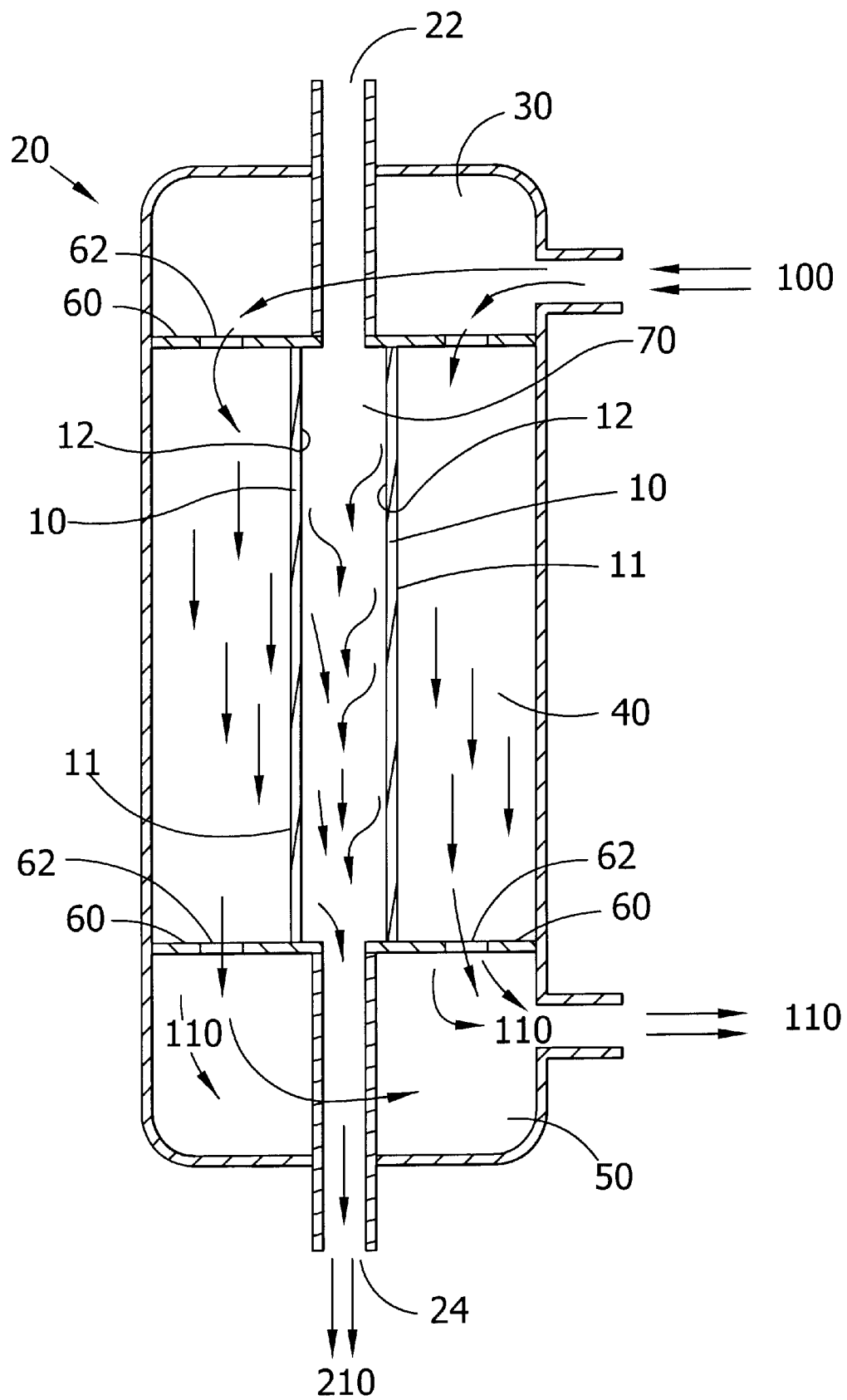
FIG. 1 is a schematic cross-sectional view of a tangential flow membrane separation unit having semipermeable membrane sheets.

In the present invention, contaminating proteins such as clotting factors are separated from a thromboplastin solution by membrane permeation. The thromboplastin solution is exposed to a semipermeable membrane and the contaminating proteins are allowed to pass from the thromboplastin solution through the membrane, while biologically active Tissue Factor is retained in the thromboplastin solution. In a preferred method, one or more contaminating clotting factors are separated by diafiltration from a thromboplastin extract of mammalian tissue, and the purified thromboplastin extract is combined with $Ca^{++}$ ions to form a thromboplastin reagent.

As used herein, the term "Tissue Factor" refers to an integral membrane glycoprotein that is biologically active for initiating blood coagulation through the extrinsic pathway. Tissue Factor comprises a protein component, referred to herein as "Tissue Factor protein," and a lipid component. The lipid component of Tissue Factor primarily comprises phospholipids. Tissue Factor can be naturally occurring Tissue Factor, such as that included in mammalian tissue extracts, or, alternatively, can be synthetically prepared, for example, by combination of isolated or recombinantly produced Tissue Factor protein and phospholipids at appropriate ratios. See U.S. Pat. No. 5,017,556 and references cited therein.

The term "thromboplastin solution", as used herein, is a solution that comprises biologically active Tissue Factor and one or more plasma clotting factors—regardless of the manner in which the solution is prepared and regardless of whether other components are present in the solution. As such, the term "thromboplastin solution" includes within its scope a "thromboplastin extract" and a "thromboplastin reagent", defined as follows. A "thromboplastin extract", as used herein, refers to a thromboplastin solution comprising biologically active Tissue Factor and one or more plasma clotting factors where the Tissue Factor is obtained as an extract from mammalian tissue. A "thromboplastin reagent", as used herein, refers to a thromboplastin solution comprising biologically active Tissue Factor, one or more plasma clotting factors and calcium ions, $Ca^{++}$, without regard to the source or method of preparation of the Tissue Factor.

While the separation approach disclosed herein is applicable to any thromboplastin solution, plasma clotting factors are preferably separated from a thromboplastin extract—prior to the formation of a $Ca^{++}$-containing thromboplastin reagent. The thromboplastin extract can be prepared by any of the many protocols known in the art and/or later developed. The thromboplastin extract can be freshly prepared, can be prepared, stored frozen, and thawed, or can be otherwise preserved with respect to its procoagulant activity.

The thromboplastin extract can be prepared by extracting Tissue Factor from mammalian tissues. The mammalian tissues can be tissues of any mammals having extractable biologically active Tissue Factor, including, for example, brain, lung and/or placenta of humans, rabbits, bovine, swine and/or non-human primates. Rabbit brain, human brain and human placenta are preferred tissue sources for the thromboplastin extract. The tissue may be washed prior to extraction to remove residual blood. The tissue to be extracted can be whole tissue or homogenized tissue, and can, if desired, be dehydrated tissue. Exemplary forms of dehydrated tissue include solvent powders (e.g. an acetone powder) of the tissue or lyophilized tissue. Such dehydrated tissues are commercially available from, for example, Sigma Chemical, St. Louis, Mo. A most preferred tissue source is rabbit brain acetone powder (RBAP).

The mammalian tissue is contacted with a solution, preferably with a salt solution, and most preferably with an aqueous solution of inorganic and/or organic salts, to extract Tissue Factor from the tissue. The extraction solution preferably has an essential absence of calcium ions. Preferred aqueous extraction solutions comprise a chloride salt and/or a lactate, an acetate or a citrate salt. An aqueous solution comprising sodium chloride and sodium citrate is a most preferred extraction solution. See, for example, Examples 1 and 2. In the preferred extraction solution, the concentration of sodium citrate ranges from greater than 5 mM to about 50 mM, more preferably from about 7 mM to about 15 mM, and is most preferably about 13 mM. When used in combination with an inorganic salt (e.g. NaCl), the molar ratio of sodium citrate to the inorganic salt preferably ranges from about 1:10 to about 1:1, and is preferably about 1:5. Extraction with an extraction solution comprising sodium citrate is advantageous over the use of calcium citrate or other calcium salts because calcium—unlike sodium—facilitates complex formation between certain plasma clotting factors (e.g. Factor VII) and Tissue Factor.

If desired, extraction of the tissue can also be effected in the presence of detergents, (e.g. nonionic detergents such as Triton® X-100), chaotropic agents (e.g. thiocyanate), and/or absorbers (e.g. $BaSO_4$) as taught in U.S. Pat. No. 5,270,451 to Hawkins et al. See, for example, Example 3D. The extraction solution can also comprise, alternatively or in combination, metal-chelators (e.g. ethylenediaminetetraacetic acid (EDTA)), as taught in U.S. Pat. No. 5,391,380 to Barrows et al. See, for example, Example 3D. As discussed below, however, such chelators are preferably added to the thromboplastin extract after extraction, but prior to membrane separation, and are, moreover, preferably employed at higher concentrations than those taught by Barrows et al.

While the extraction pH, temperature and duration are not of critical importance and are within the general skill of the art, the extraction is preferably effected at a pH ranging from about 6.5 to about 8.5, and preferably about 8.0, at a temperature ranging from about 30° C. to about 50° C., and preferably at about 45° C. for a period of time ranging from about 10 minutes to about 1 hour, and preferably for about 15 minutes. The extraction mixture is preferably stirred and/or otherwise agitated during the extraction. Following extraction, the thromboplastin extract solution is separated from the residual extracted tissue, preferably by centrifugation.

The stability of the thromboplastin extract can be improved by combining the extraction solution or the resulting thromboplastin extract with a phospholipase inhibitor. Without being bound by theory not specifically recited in the claims, phospholipase contaminants present in the thromboplastin extract are believed to have an adverse effect on procoagulant activity of the extract as it ages. A preferred phospholipase inhibitor is D609. See Example 5, regarding experimental data relating to phospholipase inhibitors.

Contaminating proteins are, in one embodiment, separated from the thromboplastin solution, and preferably from a thromboplastin extract, after treatment of the thromboplastin solution with a proteolytic enzyme. The proteolytic enzyme preferably has proteolytic activity against the contaminant proteins, but is not substantially active against Tissue Factor, and as such, does not substantially affect the procoagulant activity of the Tissue Factor. Chymotrypsin is a preferred proteolytic enzymes. The contaminant protein in the thromboplastin extract is enzymatically digested to form contaminant protein fragments. In a preferred approach employing chymotrypsin (1018 U/mg), the chymotrypsin concentration ranges from about 1 $\mu$g/ml to about 10 $\mu$g/ml, preferably from about 1 $\mu$g/ml to about 5 $\mu$g/ml, and is most preferably about 3 $\mu$g/ml is added to the thromboplastin extract and incubated at room temperature overnight. However, other concentrations, temperatures and incubation periods may be suitably employed. The digested contaminant protein fragments can then be separated from the thromboplastin extract to form a purified thromboplastin extract. Such separation is preferably effected by membrane permeation, as discussed below. See Example 5, regarding experimental data relating to enzymatic digestion of contaminant proteins.

Contaminating proteins, including digested contaminant protein fragments and undigested contaminant proteins, can be separated from the thromboplastin solution, and preferably from a thromboplastin extract, by membrane permeation. See, for example, Examples 3A through 3F. As used herein, the term "membrane permeation" refers to a separation process in which a first molecular species (e.g. a clotting factor) in a feed solution is transported through a semipermeable membrane due to differences in concentration and/or pressure across the membrane, but a second molecular species (e.g. Tissue Factor) in the feed solution is either not transported through the membrane or is transported at a slower rate, whereby separation of the first and second molecular species is effected. See, generally, Perry's Chemical Engineers' Handbook, 6th Ed., pp. 17/14–17/33, McGraw-Hill (1984). Solvent from the feed solution may also accompany the clotting factor through the semipermeable membrane.

The proteins being separated from the thromboplastin solution are preferably plasma clotting factors. In particular, it is advantageous to separate one or more plasma clotting factors that affect the extrinsic coagulation pathway— including primarily vitamin K-dependent clotting factors (e.g. Factor VII, Factor II, Factor X, Factor IX, Factor XI and Factor XII), Protein C, Protein S and Protein Z. It is especially desirable to separate at least Factor VII from the thromboplastin solution. Other contaminating proteins, such as hemoglobin (Hb), can also be effectively separated according to the methods of the present invention. Preferably, each of the aforementioned plasma clotting factors are separated from the thromboplastin solution simultaneously in a single operation. However, a series of process operations can be used, if desired, to selectively separate such contaminating proteins. Moreover, a complete separation of all of a particular type of clotting factor is not essential to obtain the benefits of the present invention. Rather, even a partial separation/removal of a particular clotting factor (e.g. Factor VII) can improve the sensitivity of the thromboplastin reagent to a commercially-significant extent.

In addition to the thromboplastin solution, the feed solution can also comprise separation-enhancing additives that facilitate separation of one or more plasma clotting factors from the thromboplastin solution, and particularly, from Tissue Factor. Without being bound by theory, contaminating plasma clotting factors associated with extracted Tissue Factor can be considered as being either free clotting factors dissolved in the extraction solution or, alternatively, clotting factors complexed with the relatively large Tissue-Factor-associated vesicles. As such, separation-enhancing additives that can disrupt the complexed clotting factors to make them more susceptible to separation can be advantageously employed. For example, Factor VII is known to complex with Tissue Factor in a calcium-dependent manner. As such, it is preferable to include a calcium chelating agent, such as ethylenediaminetetraacetic acid (EDTA) or salts thereof in the feed solution, to reduce the affinity between Factor VII and Tissue Factor. See, for example, Example 3B. Other calcium chelating agents, such as citrate, citrate salts, and ethylenebis(oxyethylenenitrilo)tetraacetic acid may likewise be used. EDTA is a preferred calcium-chelator and is preferably included in the feed solution at concentrations ranging from about 1 mM to about 50 mM, more preferably ranging from about 5 mM to about 20 mM, and most preferably at about 10 mM. If the thromboplastin solution is a thromboplastin extract and if a metal-ion chelator such as EDTA was included in the extraction solution, then additional EDTA may not be required to reduce the Factor VII-Tissue Factor affinity. Other dissociation agents, such as detergents, chaotropic agents, buffers and the like may also be included in the feed solution. Non-ionic detergents such as Triton X-100® and/or CHAPS can be suitably employed. See, for example, Example 3D.

If desired, the membrane permeation process may also involve a dilution solution and/or a carrier solution. A dilution solution is employed in processes where solvent from the feed solution is allowed to transfer through the membrane with the clotting factor. The dilution is used to make-up or redilute the feed solution as the solvent is removed therefrom. A carrier solution is employed on the opposing side of the membrane relative to the feed solution. Carrier solutions are typically employed in diffusion-based mass-transfer processes driven by concentration differences, and are not necessary in pressure-driven processes where solvent from the feed solution is allowed to transfer through the membrane with the clotting factor. Nonetheless, carrier solutions can be employed, if desired, even in such processes. The carrier solution, if employed, can have a concentration of contaminant proteins (e.g. plasma clotting factors) that is less than the concentration thereof in the feed solution (to allow for concentration-driven mass transfer) and/or can be maintained at a lower pressure relative to the pressure of the feed solution (to allow for solvent-flow mass transfer). In any case, the dilution solution and/or carrier solution can be any liquid suitable for entraining and/or receiving the clotting factor, respectively, as it passes through the semipermeable membrane. Water and aqueous solutions are preferred dilution and/or carrier solutions. The dilution solution and/or carrier solution is preferably matched with the feed solution as closely as possible except with respect to the involved solutes to be separated in the process: Tissue Factor and one or more plasma clotting factors. Hence, when the thromboplastin solution being purified is a thromboplastin extract (as is preferred), the dilution/carrier solution can be the same type of solution that was employed as the extraction solution (prior to extraction).

The particular membrane separation protocol used to effect the separation is not narrowly critical, and can include, for example, dialysis, osmosis, reverse osmosis, ultrafiltration, diafiltration, electrodialysis and the like. As discussed below, macrosolute-fractionation protocols such as ultrafiltration or diafiltration are preferred membrane separation processes. Each such membrane separation protocol generally involves exposing the thromboplastin feed solution to a first surface of a semipermeable membrane and collecting the exposed feed solution as a retentate. The concentration of a protein contaminant of interest (e.g. a plasma clotting factor) in the retentate is lower than in the feed solution. Additionally, the second surface of the membrane is typically exposed to either a carrier solution or to solvent that originates from the feed solution and passes through the membrane with the contaminant protein. In either case, the liquid exposed to the second surface of the membrane is referred to as a permeate. If a carrier solution is used, the permeate is enriched in the protein contaminant being separated relative to the carrier solution.

The semipermeable membrane can comprise any material through which one or more plasma clotting factors passes preferentially relative to Tissue Factor. Plasma clotting factors have molecular weights of about 60,000 Daltons (60 kD). Tissue Factor is somewhat heterogeneous with respect to molecular weight: about 90% of Tissue Factor has a molecular weight of greater than 1 million Daltons (1000 kD), and 80% of Tissue Factor has a molecular weight of less than about 2 million Daltons (2000 kD), based on membrane separation studies with 1000 kD and 2000 kD membranes, respectfully. Accordingly, the semipermeable membrane employed should have a nominal molecular weight cutoff (MWCO), as characterized using industry-standard globulin-like proteins, ranging from at least about 75,000 Daltons (75 kD) to about 2 million Daltons (2000 kD), more preferably ranging from at least about 100,000 Daltons (100 kD) to about 1 million Daltons (1000 kD), even more preferably ranging from at least about 100,000 Daltons (100 kD) to about 500,000 Daltons (500 kD), and most preferably ranging from about 200,000 Daltons (200 kD) to about 400,000 Daltons (400 kD). The semipermeable membrane most preferably has, a nominal molecular weight cutoff, as characterized using industry-standard globulin-like proteins, of about 300,000 Daltons (300 kD). However, as known industrial applications involving membrane separations of other solutes can involve membranes having a nominal molecular-weight cut-off value of ten times the molecular weight of the solute to be passed through the membrane or more, MWCO values up to about 600,000 Daltons (600 kD) or higher may be determined to be more useful after optimization studies are performed by a skilled artisan for a particular application of the present invention. Considered with respect to passage and retention of the involved solutes, the semipermeable membrane of the present invention should have a MWCO sized to allow at least about 25%, preferably at least about 50%, more preferably at least about 75%, even more preferably at least about 90%, yet more preferably at least about 95% and most preferably at least about 99% of the detectable plasma clotting factors of interest to pass through the membrane while simultaneously retaining at least about 10%, preferably at least about 25%, more preferably at least about 50%, even more preferably at least about 75%, still more preferably at least about 90%, yet more preferably at least about 95%, and most preferably at least about 99% of detectable biologically active Tissue Factor. A most preferred semipermeable membrane will allow 100% of the detectable plasma clotting factor of interest to pass while retaining 100% of the detectable active Tissue Factor.

A number of semipermeable membranes having MWCO's within the preferred ranges described above and suitable for use in connection with the present invention are known in the art and commercially available. Such semipermeable membranes are preferably solid membranes and are typically polymeric in nature, but are not limited to such for purposes of the present invention. Polymeric membranes can be of natural polymers or synthetic polymers, and may be crystalline and/or amorphous in structure. Exemplary polymeric membrane materials include cellulosic polymers, polyamides, polysulfones, polyacrylonitriles, polyfurans, polyalkenes, polyacetates, polyvinyls, and copolymers of the same, among others. A polyethersulfone membrane is a suitable membrane material. The membranes may be in various forms or designs, such as "sheets", "hollow fibers", "thin-channel" and "parallel-leaf" designs, and may be symmetric or asymmetric. Selection of a particular membrane, including choice of material(s), form, symmetry, pore size, pore density (porosity), permeability, chemical stability, thermal stability and mechanical stability (e.g. for cleaning) for use in connection with the applications described herein is within the ordinary skill in the art. If desirable, membranes can be pretreated and/or treated "in-line" with swelling agents, stretched, thermally treated, and or chemically reacted, to control, for example, porosity and pore size—parameters that affect overall transfer rates. Preferred semipermeable membranes include the DispoDialyzer® (Spectrum) and the Pellicon XL® (Millipore) which are available with the preferred 300 kD MWCO size as well as with other MWCO sizes.

The particular physical configuration for the semipermeable membrane is not narrowly critical. The semipermeable membrane can be assembled as a module in various designs such as "shell and tube", "plate and frame", "stack", "biflow stack" and "spiral-wound", among others. See Perry's Chemical Engineer's Handbook, supra. Larger scale commercial designs are typically "tank" types, in which the feed solution is circulated through a tank around flat semipermeable membrane bags which include the carrier solution, "filter-press" types, in which vertical membranes are sandwiched between alternate feed solution and carrier solution frames, or "shell-and-tube" types in which tubular membranes (e.g. hollow-fiber membranes) are configured within a shell with the feed solution passing through the tubes and the carrier solution, if employed, passing through the shell.

The semipermeable membrane can be of a form and configuration suitably designed for various separation protocols, various flow regimes, and various operational approaches. More specifically, the membrane and/or membrane module design can be suitable for separations effected based primarily on concentration differences across the membrane (e.g. as in dialysis-type permeation processes) or based on pressure differences across the membrane (e.g. as in ultrafiltration-type permeation process). The membrane and/or membrane module design can allow for various types of flow regimes of the thromboplastin solution relative to the membrane surface, including, for example, direct or impinging flow or tangential flow regimes. A design which allows the feed solution to flow tangentially across the surface of a semipermeable membrane is generally preferred, as such a design reduces the extent of plugging of membrane pores due to the "sweeping" action of the feed solution. Where a carrier solution is employed, the membrane and/or membrane module design can also allow for various types of flow regimes of the thromboplastin solution relative to the membrane surface, including, parallel flow, cross flow, or counter flow regimes. With respect to operational considerations, the membrane and/or membrane module design can be suited for batch, semicontinuous (e.g. feed and bleed), or continuous operation.

An exemplary tangential-flow semipermeable membrane module includes, with reference to FIG. 1, two membrane sheets 10 configured into a tangential flow-type separation unit 20, having entrance-end bell 30, mid-section 40 and exit-end bell 50. Plates 60 separate the mid-section 40 from the entrance-end bell 30 and exit-end bell 50. Each membrane sheet 10 has a first surface 11 and a second surface 12. A feed solution 100 that comprises the thromboplastin solution is supplied through the entrance bell 30 of the unit 20 and flows to the mid-section 40 through apertures 62 in plates 60. In the mid-section 40, the feed solution 100 contacts the first surface 11 of each membrane sheet 10. While not shown in FIG. 1, a carrier solution can simultaneously be supplied through carrier entrance port 22 of the unit 20 to be exposed to the second surface 12 of the membrane sheets 10. Regardless of whether a carrier solution is supplied to the unit 20, one or more clotting factors in the feed solution 100 and, in a preferred embodiment, solvent from the feed solution 100, pass through the membrane sheets 10 to the space 70 between the membrane sheets 10, while Tissue Factor is retained in the feed solution. The clotting-factor-depleted feed solution, now referred to as a retentate 110, is discharged from the mid-section 40 through the exit-end bell 50 of the unit 20. The discharged retentate 110 is depleted of clotting factor relative to the feed solution 100. The clotting-factor-carrying solvent, referred to as permeate 210, is discharged from mid-section 40 of the unit 20 through permeate exit port 24.

Figure 2:
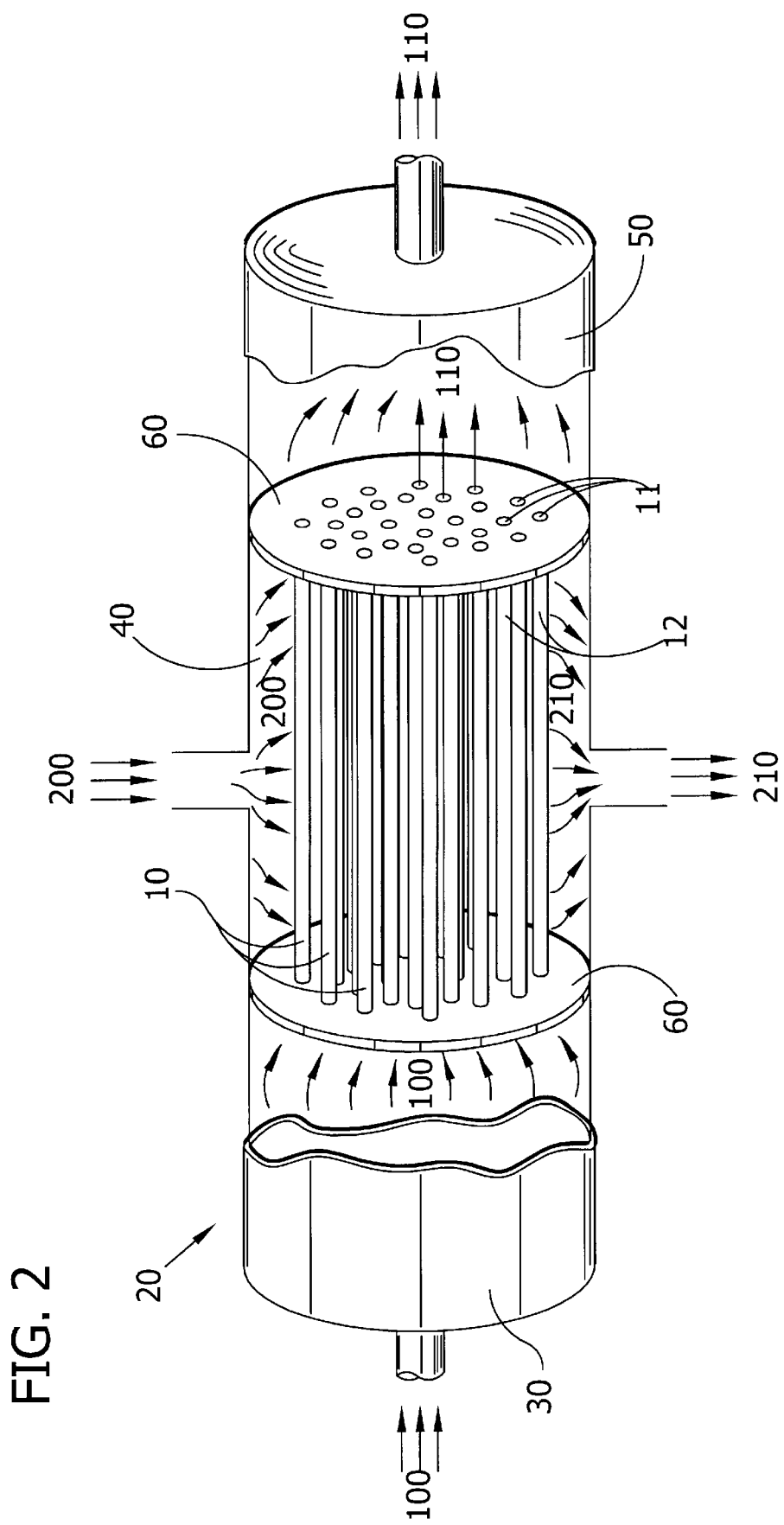
FIG. 2 is a perspective view of a shell-and-tube type membrane separation unit having tubular semipermeable membranes.

In another exemplary configuration, with reference to FIG. 2, the semipermeable membrane can be a tubular-type (e.g. hollow-fiber or thin-channel) membrane 10 configured into a shell-and-tube type separation unit 20, having entrance-end bell 30, mid-section 40 and exit-end bell 50. Tube plates 60 separate the mid-section 40 from the entrance-end bell 30 and exit-end bell 50. Each membrane 10 has a first inner surface 11 and a second outer surface 12. A feed solution 100 that comprises the thromboplastin solution is supplied through the entrance bell 30 of the unit 20 to the inner surface 11 of the membranes 10. A carrier solution 200 can, if desired, be simultaneously supplied through the mid-section 40 of the unit 20 to the outer surface 12 of the membranes 10. One or more clotting factors in the feed solution 100 pass through the membrane to the carrier solution 200, typically accompanied by solvent from the feed solution 100, while Tissue Factor is retained in the feed solution 100. The clotting-factor-depleted feed solution, now referred to as a retentate 110, is discharged from the membranes 10 through the exit-end bell 50 of the unit 20. The clotting-factor-enriched carrier solution, now referred to as a permeate 210, is discharged from mid-section 40 of the unit 20. The discharged permeate 210 is enriched with the clotting factor relative to the carrier solution 200.

A membrane separation unit, such as the exemplary units described above, can be employed—alone or in combination with other units—in batch, semicontinuous (single-stage continuous or single-stage "feed and bleed"), or multi-stage continuous processes to effect separation of the clotting factor from Tissue Factor.

Figure 3:
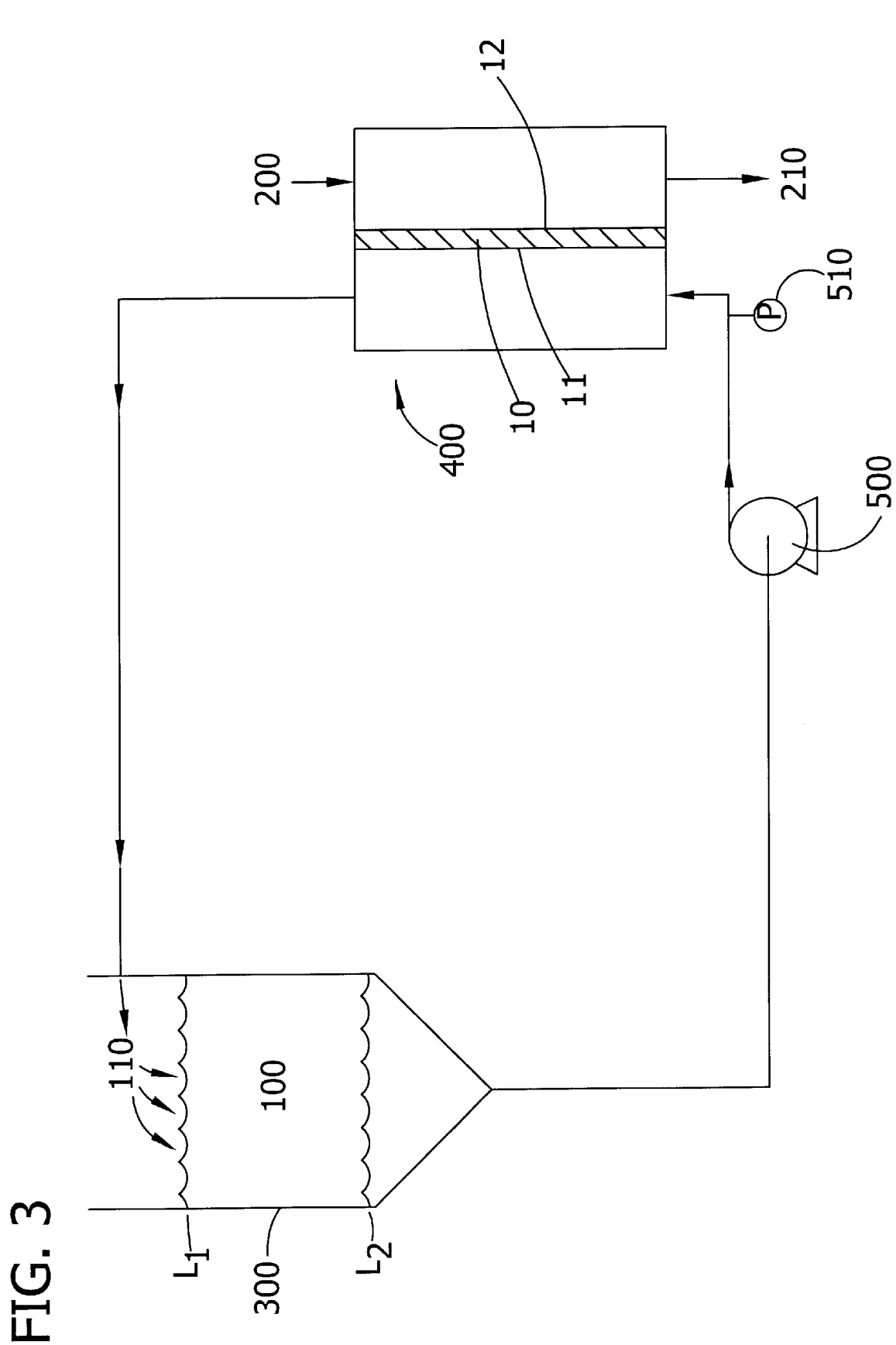
FIG. 3 is a schematic diagram of a single-stage membrane separation process configured for batch operation.

In a preferred batch process, a thromboplastin extract is treated in a tangential-flow diafiltration. With reference to FIG. 3, a feed solution 100 comprising the untreated thromboplastin extract is continuously recirculated from a feed tank 300, passed through a membrane separation unit 400, optionally against a carrier solution 200, and then returned to the feed tank 300 by means of a pump 500. The membrane separation unit 400 comprises a semipermeable membrane 10 having a first surface 11 to which the feed solution 100 is exposed and a second surface 12 to which the carrier solution 200 is exposed. Each of the first and second surfaces 11, 12 have a surface area, A. The pressure of the feed solution 100, as determined by inlet pressure gauge 510, is greater than that on the carrier solution/permeate side of the membrane 10 and each pass through the membrane separation unit 400 results in passage of clotting factor and solvent from the feed solution 100 to the other side of the membrane 10, such that the retentate 110 being recirculated back to the feed tank 300 is depleted of clotting factor relative to the feed solution 100, and is more concentrated in Tissue Factor. The level of feed solution 100 in the feed tank 300 falls from its initial level, $L_1$, to a lower level, $L_2$, as the solvent is removed by permeation through the membrane 10. After the level in the feed tank 300 has fallen to $L_2$, the concentrated feed solution 100 can be rediluted with a dilution solution and the level raised to the initial level, $L_1$. Each cycle in which the feed tank 300 is emptied and refilled is considered, for purposes of description herein, as one dilution cycle. If desired, the recirculation can be continued for as many dilution cycles as necessary to effectuate the desired level of separation. Other batch process configurations will be apparent to a person of skill in the art.

A design parameter in such a preferred batch separation scheme is the level of separation achieved for a unit volume of feed solution 100 passing through the separation unit 400. The incremental separation for such a unit volume is generally a function of the type of semipermeable membrane 10 (or module) being employed in the unit 400, with important design considerations being MWCO, permeability, total area, A, flow-regime, and configuration, as discussed above. For a given separation unit 400, the incremental separation and overall separation achievable over a period of time can be evaluated using bench-scale studies. A parameter to be considered in bench-scale studies for such a preferred batch process is the permeate flux rate (volume of permeate passing through a unit surface area of membrane per unit time), which, in turn, is dependent upon the pressure-differential across the membrane 10. The pressure differential can be controlled by adjusting the pump 500 and corresponding volumetric flow rate of the recirculating feed solution 100. For evaluating overall separation, the volume of feed solution being processed, the volume differential of the feed tank 300 per cycle (ie, the dilution volume), the number of cycles, the time per cycle, and the total time for achieving a particular degree of separation are also parameters to be determined. The process control parameters can be varied by a skilled artisan, as necessary, to optimize separation process.

In exemplary bench-scale studies involving the preferred batch process outlined above, 100 ml of a $Na_3$Citrate/NaCl thromboplastin extract were diafiltered through a tangential-flow Pellicon XL® (Millipore) 50 cm² cassette with a 300 kD MWCO using a $Na_3$Citrate/NaCl dilution solution. In a first study, recirculation flow rate was adjusted to obtain an inlet pressure of about 10 psig—resulting in a membrane flow rate of about 100 ml/hr (corresponding to a membrane flux of about 4 ml/cm² hr). The original feed solution was diluted about 100 fold in a total time of about 5 hours using 5 dilution cycles, each of which effected about a 2.5-fold dilution of the feed solution. See, for example, Example 3B. In a second study, in which the recirculation flow rate was changed to obtain an inlet pressure of about 20 psig—resulting in a membrane flow rate of about 200 ml/hr (corresponding to a membrane flux of about 8 ml/cm²hr), a 100-fold dilution in the feed solution was achieved in a total time of about 3 hours, with 3 dilution cycles in which each cycle effected about a 5-fold dilution in the feed solution. See, for example, Example 3B. Comparison of the operating parameters of the two bench-scale experiments suggests that a higher membrane flow rate can achieve results comparable to the lower rate, with either (1) a 50% reduction in processing time using the same membrane surface area (and a corresponding reduction in operating costs), or (2) with the same time but using a 50% reduction in membrane surface area (and a corresponding reduction in capital costs). A batch pilot-plant study was scaled up based on these bench-scale studies.

Figure 4:
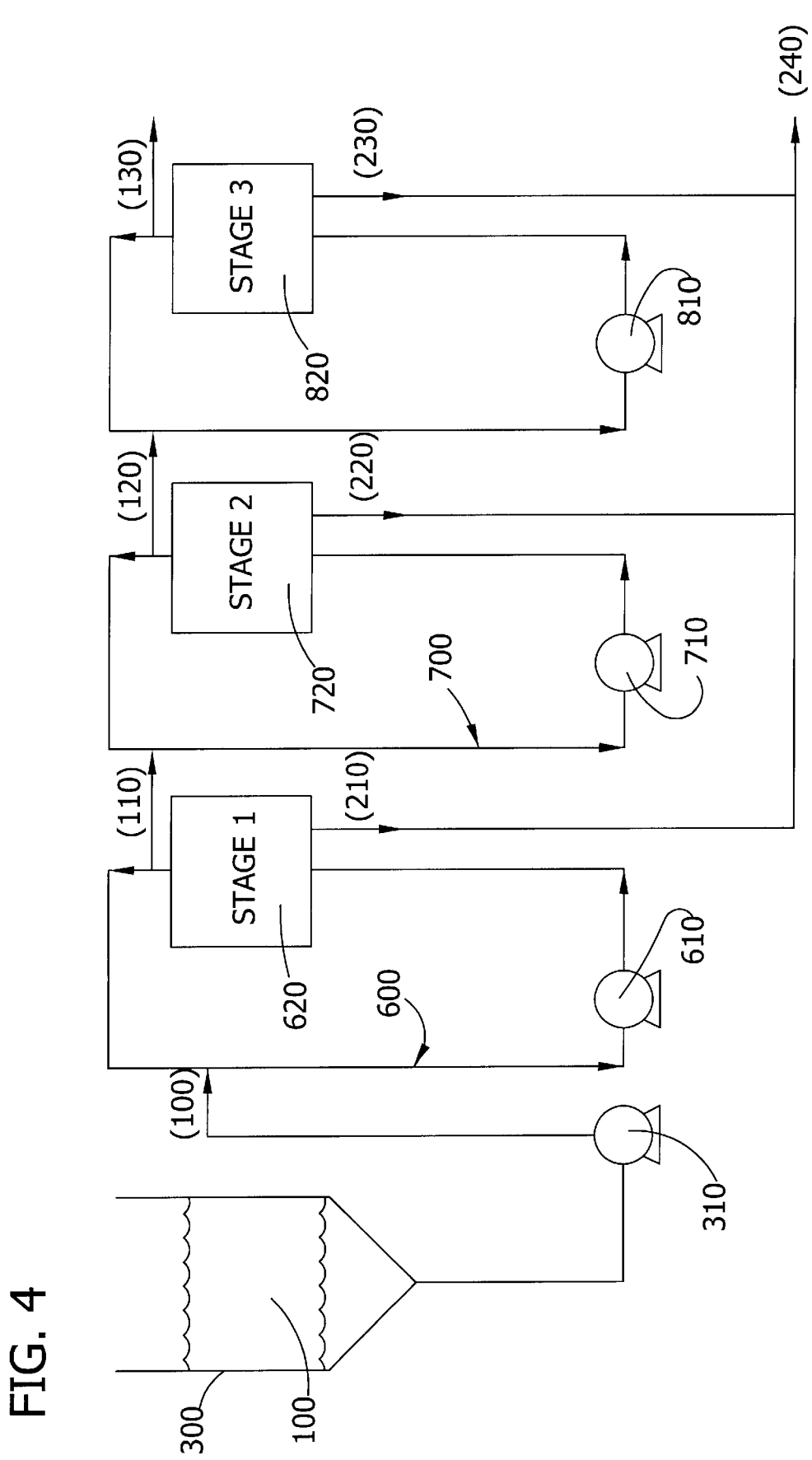
FIG. 4 is a schematic diagram of a multiple-stage membrane separation process configured for continuous feed-and-bleed operation.

While the aforementioned description involves a batch process approach, the invention can also be employed in semicontinuous or continuous processes. In an exemplary semicontinuous process based on the batch process shown in FIG. 3, the level in the feed tank 300 can be maintained as constant (e.g. at $L_1$) by continuously adding dilution solution to the feed tank 200 at a rate that is equal to the solvent flow rate through the semipermeable membrane 10. In an exemplary "feed and bleed" continuous process, shown schematically in FIG. 4, a feed solution 100 is pumped from a feed tank 300 by means of feed pump 310 to a first stage recirculation loop 600. A first recirculation pump 610 recirculates a first stream through a first separation unit 620, with the permeate 210 being discharged through a combined discharge header, the bulk of the retentate 110 being recirculated through the loop 600 and a relatively small portion of the retentate 110 being bled off to supply a second recirculation loop 700. A second recirculation pump 710 recirculates a second stream through a second separation unit 720, with the permeate 220 being discharged through a combined discharge header, the bulk of the retentate 120 being recirculated through the loop 700 and a relatively small portion of the retentate 120 being bled off to supply a third recirculation loop 800. A third recirculation pump 810 recirculates a third stream through a third separation unit 820, with the permeate 230 being discharged through a combined discharge header, the bulk of the retentate 130 being recirculated through the loop 800 and a relatively small portion of the retentate 130 being bled off as purified thromboplastin extract. Each stage operates at nearly constant concentration of the retained solute, Tissue Factor, with the latter stages having relatively higher concentrations of Tissue Factor than the earlier stages. Other semicontinuous and continuous process configurations will be apparent to a person of skill in the art.

If the thromboplastin solution being purified by membrane permeation is a thromboplastin reagent, then the reagent can be employed in a PT assay directly or upon addition of further ingredients discussed below in connection with the preparation of reagent from thromboplastin extract. If the thromboplastin solution being purified by membrane permeation is a thromboplastin extract, then a thromboplastin reagent may be prepared from the purified thromboplastin extract as follows.

A thromboplastin reagent can be prepared from the purified thromboplastin extract, alternatively referred to herein as a treated extract, by combining the treated extract with calcium ions, $Ca^{++}$. The amount of treated extract in the reagent composition preferably ranges from about 10% to about 50% by volume relative to the total volume of the reagent composition, more preferably from about 15% to about 45% by volume, and most preferably from about 25% to about 35% by volume. In a preferred reagent composition, the amount of treated extract is about 30% by volume. The calcium ions can be supplied to the reagent composition as a calcium salt such as calcium chloride, $CaCl_2$, or a calcium salt of an organic acid, such as calcium tartrate, calcium gluconate, calcium citrate and calcium lactate. The calcium is preferably supplied as $CaCl_2$ and employed in the reagent composition at a concentration ranging from about 10 mM to about 15 mM, more preferably at a concentration ranging from about 10 mM to about 12 mM, and most preferably at about 11 mM.

Other reagent components such as buffers, stabilizers, preservatives, sensitizing agents and bulking agents can also be included in the thromboplastin reagent composition. Buffers can be employed to maintain the reagent composition at a pH ranging from about 6.8 to about 8.0 and preferably at a pH of about 7.5. Exemplary buffers include for example, Tris, phosphate, barbital, glycylglycine, 3-(N-morpholino)-propanesulfonic acid (MOPS), N,N-bis-(hyrdroxyethyl)-2-aminoethanesulfonic acid (BES), N-tris-(hyrdroxymethyl)-methyl-2-aminoethanesulfonic acid (TES), N-2-hydroxyethyl piperazine-N-2-ethanesulfonic acid (HEPES), 3-[N-tris(hydroxymethyl)methylamino]-2-hydroxypropanesulfonic acid (TAPSO) and 3-[N-tris-(hydroxymethyl-methylamino]-propanesulfonic acid (TAPS), among others. HEPES is a preferred buffer. Stabilizers useful in maintaining the procoagulant activity of the thromboplastin reagent are known in the art and include, for example, Goods buffers, Tris, bovine serum albumin (BSA), piperazine-N,N-bis(2-ethane-sulfonic acid, 1.5 sodium salt (PIPES), imidazole, 3-(N-morpholino)-2-hydroxypropanesulfonic acid (MOPSO), MOPS, BES, TES, HEPES, TAPSO, TAPS, 3-[N-bis(hydroxyethyl)amino]-2-hydroxypropanesulfonic acid (DIPSO), piperazine-N,N'-bis (2-hydroxypropanesulfonic acid (POPSO), N-hydroxyethyl piperazine-N'-2-hydroxypropanesulfonic acid (HEPPSO), tricine and bicine. HEPES and BSA are preferred stabilizing agents. Preservatives that prevent growth of microorganisms, such as antifungal, antibacterial and antiyeast compositions, may also be included in the reagent composition. Exemplary preservatives include sodium azide, thimerosal, BHA, BHT and preformulated multiactivity formulations such as ProClin™ (Supelco). ProClin™ is a preferred preservative. A variety of sensitizing agents are known in the art. For example, salts such as sodium chloride, can be used to improve the sensitivity of the reagent, typically in conjunction with normal-shifting reagents, such as polyethyleneglycol (PEG). Other sensitizing reagents, such as hexadimethrine bromide or protamine can be used to inhibit potentially interfering activities such as heparin activity. Bulking agents that can be included in the reagent composition include alcohols (e.g. glucitol, mannitol, sorbitol), glycine, dextrose and the like. The reagent composition can also include surfactants (e.g. Tween 80 or Triton X-100) and other agents commonly employed in plasma assays. The concentrations of these additional reagent components can be determined and optimized by a person of skill in the art.

Calcium buffering agents are also preferably added to the thromboplastin reagent composition. Significantly, the sensitivity of the thromboplastin reagent can be controlled by using such calcium buffering agents in the thromboplastin reagent. Moreover, such control is achieved with only minimal effect on clotting times for normal plasmas. Without being bound by theory not specifically recited in the claims, the calcium buffering agents modulate the concentration of free calcium in the thromboplastin reagent. Suitable calcium buffering agents include organic acid salts such as citrate or tatrate, calcium chelators such as EDTA or EGTA, and calcium binding buffers such as N-2-acetamido1-2-iminodiacetic acid (ADA), N,N-bis(2-hydroxyethyl)glycine (bicine), MES, ACES, tricine and glycylglycine. Other calcium buffering agents known or later developed in the art may likewise be employed. Sodium citrate, ADA and bicine are preferred calcium buffering agents, with sodium citrate being most preferred. The concentration of the calcium buffering agent in the thromboplastin reagent composition can vary depending on the particular calcium buffering agent employed, the concentration of other reagent components, including in particular the concentration of extract and the concentration of $Ca^{++}$ ions, and the desired sensitivity. Preferably, however, the calcium buffering agent concentration can range from about 0.25 mM to about 15 mM, more preferably from-about 0.5 mM to about 10 mM, and most preferably from about 0.5 mM to about 7 mM. In a preferred embodiment employing sodium citrate as the calcium buffering agent, the sodium citrate concentration preferably ranges from about 0.5 mM to about 7 mM, more preferably from about 1 mM to about 5 mM, and most preferably from about 2.5 mM to about 4.5 mM. With respect to such calcium buffering agents, reference is made to the experimental data of Experiment 6.

The thromboplastin reagent can be maintained in any form in which it will retain its procoagulant activity. For example, the thromboplastin reagent can be sold as a solution or in dehydrated form (e.g. lyophilized form). If desired, the thromboplastin reagent can be stored frozen at −20° C. for up to about 6 months or in another is suitable manner known in the art.

A thromboplastin reagent prepared according to the present invention preferably comprises a treated NaCl/Na$_3$Citrate thromboplastin extract (30% to 45%, most preferably 35% by volume), CaCl (10 mM to 13 mM, most preferably 11 mM), HEPES (5 mM to 50 mM, most preferably 10 mM), NaCl (70 mM to 120 mM, most preferably 80 mM), PEG 8000 (0.5% to 1.0%, most preferably 0.75% by weight/volume (assuming a solution density of 1 g/ml), additional Na$_3$Citrate (2.5 mM to 4.5 mM, most preferably 3.5 mM), hexadimethrine bromide (5 mg/l to 20 mg/l, most preferably 12.5 mg/L), mannitol (0.5% to 5%, most preferably 2% by weight/volume), glycine (0.5% to 5%, most preferably 4% by weight/volume), BSA (0.1% to 3%, most preferably 1% by weight/volume) and ProClin™ 300 (0.01% to 0.07% by weight/volume). See, for example, Examples 4 and Experiment 6. Note that ProClin volatilizes if the reagent solution is subsequently lyophilized. As demonstrated in Example 4, such thromboplastin reagents have normal PT times within commercially acceptable ranges.

Other formulations for the thromboplastin reagent are within the scope of the present invention. Such formulations will preferably, based on present commercial needs, have normal PT times ranging from about 9.0 seconds to about 20 seconds, more preferably from about 9.0 seconds to about 13.0 seconds and most preferably from about 10.0 seconds to about 12.0 seconds. Such formulations will also preferably have sensitivities as follows with respect to various of the characterizing criteria, considered independently, in various combinations or cumulatively: a dynamic range for a coumarinized plasma having an International Normalized Ratio of about 3.0 of at least about 20 seconds, more preferably at least about 30 seconds, and most preferably of at least about 40 seconds; a dynamic range for a 99%$^+$ Factor-VII-deficient plasma of at least about 30 seconds, preferably at least about 35 seconds and most preferably at least about 40 seconds; a dynamic range for a 50% pooled-normal plasma (PNP), versus a 100% PNP, ranging from about 3 seconds to about 6 seconds, and more preferably from about 4 seconds to about 5 seconds; and an International Sensitivity Index (ISI) of not more than about 2.0, preferably not more than about 1.4, and most preferably not more than about 1.25. Moreover, the methods for reproducably preparing such reagents are commercially viable.

The improved sensitivities of the thromboplastin reagents of the invention arise from, without being bound by theory not specifically recited in the claims, removal of contaminating clotting factors and other contaminating proteins from the thromboplastin solution by membrane permeation. See Example 3C. Without such removal, contaminating plasma clotting factors are present in higher concentrations in a sample and contribute to faster clotting times and lowered sensitivities. For example, Factor VII contamination present in the reagent solution would result in lowered sensitivity for determining whether a patient plasma has a Factor VII deficiency, because the contaminating Factor VII would, in effect, partially compensate for some of the deficiency. The contribution of the contaminating clotting factors and the resulting effect on clotting time is proportionally more significant for a factor-deficient plasma sample (e.g. a deficient patient plasma or a standard abnormal plasma used to determine sensitivity) than for a normal plasma sample. As such, the influence of the treated thromboplastin solution on abnormal plasma results in longer PT-clotting times, whereas the influence on normal plasmas is less substantial and results in little or no shift in normal PT-clotting time.

In addition to achieving reproducibly improved sensitivity while maintaining acceptable PT-normal times, such reagents have an improved appearance compared to known thromboplastin reagents. These reagents are visually characterized as being of an off-white milky-type appearance. Without being bound by theory, the more appealing reagent appearance appears to be based on separation of residual hemoglobin (Hb) contaminants from the thromboplastin solution by membrane permeation during the purification process outlined above. Hb is a tetrameric protein having a molecular weight of about 64,000 Daltons (64 kD) and, as such, would be separated from Tissue Factor in the same manner as plasma clotting factors, as discussed above. The level of Hb in the reagent can be determined by hemoglobin assay (for example, Sigma Diagnostics Procedure No. 527), and is preferably less than about 2.0 mg/dl, more preferably less than about 1.0 mg/dl, even more preferably less than about 0.5 mg/dl, and most preferably not detectable using the Sigma Diagnostic Procedure No. 527 assay. See, for Example, the experimental data included as Experiment 7.

The thromboplastin reagents of the present invention can be used in a variety of diagnostic applications known in the art. Preferably, the thromboplastin reagents are used in assays based on clotting times, such as prothrombin-time (PT) assays. Such assays typically involve the determination of clotting time—that is, of the elapsed time as measured from the formation of an assay solution (by combination of a thromboplastin reagent and a plasma sample) to detection of clot formation in the assay solution. The time measurement and/or clot detection can be automated or carried out manually using a variety of techniques known in the art. Exemplary methods for determination of clot formation include visual observations with a "tilt-tube" technique, electrochemical methods (e.g. fibrometer), optical methods (e.g. based on absorbance or rate of change of absorbance), among others. Exemplary automated analyzers include Amelung CS-190, MLA-900.

The PT assays can be employed advantageously for determining blood coagulation deficiencies associated with the extrinsic coagulation pathway. For example, thromboplastin reagents having less Factor VII contaminants will provide more accurate screening for patients having a Factor VII deficiency. Prothrombin-time assays can also be employed for monitoring anticoagulant treatment with pharmaceuticals, such as coumarin, that affect the extrinsic coagulation pathway. Because the basis of such anticoagulation therapy is a controlled decrease in a patient's functional vitamin K-dependent proteins, the sensitive thromboplastin reagents of the present invention will provide for more precise monitoring and control of the therapeutic regimen. The reagents of the present invention can be used in qualititative screening assays, and in addition, in quantitatively determinations of the level of a plasma clotting factor present in a test plasma. Such a quantitative determination involves determining the clotting times of standard plasmas having various known levels of the plasma clotting factor and preparing a standard correlation between the clotting times of the standard plasmas and the level of the plasma clotting factor in the standard plasmas. The clotting time of a test plasma is then determined and the level of the plasma clotting factor in the sample is determined based on the standard correlation.

The following examples illustrate the principles and advantages of the invention.

EXAMPLES

Eample 1: Preparation of Extraction/Dilution/Carrier Solutions

A solution was prepared for use as an extraction solution, a dilution solution and/or a carrier solution by combining NaCl (2.92 g) and Na₃Citrate (3.93 g) with water (1000 ml) to achieve an extraction/dilution/carrier solution comprising 50 mM NaCl and 13 mM Na₃Citrate.

Example 2: Preparation of Thromboplastin Extract

A thromboplastin extract comprising active Tissue Factor was prepared by contacting 5 g of rabbit-brain acetone powder with 100 ml of the extraction solution of Example 1 for 15 minutes at 45° C. with 400 rpm mixing. Following extraction of Tissue Factor into the extraction solution, the supernatant was separated from the extracted tissue by centrifuge.

Example 3: Membrane Separation of Contaminatinq Proteins from Thromboplastin Extract, Preparation of ThromboPlastin Reagents, and Evaluation Thereof In the following experiments, the standard "normal" and "abnormal" plasma samples employed in PT assays for evaluating various thromboplastin reagents included: a "Control Level I" normal plasma (Sigma Diagnostics, C7906); a pooled-normal-plasma ("PNP"); a coumarinized plasma having an International Normalized Ratio (INR) of about 3.0; and a 99%⁺ Factor-VII-deficient plasma (Sigma Diagnostics, R7D-S). A CS-190 Optical Analyzer was used in optical mode to determine PT clotting times for the various plasma samples, except as otherwise noted.

Example 3A: Dialysis of Thromboplastin Extract (100 kD MWCO—Bench Scale)

A thromboplastin extract was prepared as described in Example 2 and dialyzed through a bench-scale DispoDyalyzer™ (Spectrum) having a MWCO of 100 kD. The dialysis was performed at a pH of 7.0 to 8.0, a temperature of 2–8° C. and atmospheric pressure, for a period of six hours against a carrier solution prepared as in Example 1.

The dialyzed extract was used to prepare a thromboplastin reagent by combining the dialyzed extract (35% by volume) with CaCl₂ (11 mM), HEPES, NaCl, PEG 8000, hexadimethrine bromide, mannitol, glycine, BSA and ProClin™ 300. The thromboplastin reagent composition was evaluated in PT assays for a pooled-normal plasma, a Level I coagulation control (Coag I), a coumarinized plasma (CP), and a 99%⁺ Factor VII-deficient plasma (F7D-1) using a CS-190 Optical Analyzer to determine PT clotting times for the various plasma samples. The results are shown in Table 3A.1

TABLE 3A.1

PT Clotting Times for Thromboplastin Reagent (35% Dialyzed Extract/100 MWCO)

| Extract | Coag I | PNP | CP | F7D-I | CP/PNP |
| --- | --- | --- | --- | --- | --- |
| undialyzed control | 11.0 | 11.1 | 26.2 | 26.6 | 2.36 |
| 100K MWCO dialysis | 10.6 | 10.6 | 26.4 | 29.9 | 2.49 |
| 300K MWCO dialysis | 10.5 | 10.5 | 26.1 | 29.4 | 2.49 |

These data demonstrate that the contaminating clotting factors were effectively removed from the thromboplastin extract by concentration-driven dialysis while biologically-active Tissue Factor was retained in the extract solution. The thromboplastin reagent prepared from the dialyzed extract had procoagulant activity and offered an increase in reagent sensitivity as evidenced by an increase in the CP/PNP ratio, an increase in the dynamic range for the Factor VII-deficient plasma, and only a moderate affect on PT normal times.

Example 3B: Diafiltering of Thromboplastin Extract (300 kD MWCO/EDTA—Bench Scale)

A thromboplastin extract was prepared as described in Example 2 and 100 ml of extract was then combined with EDTA (10 mM) to form an extract/EDTA solution.

In a first bench-scale experiment, the extract/EDTA solution was diafiltered through a bench scale Pellicon XL™ (Millipore) 50 cm² cassette having a polyethersulfone membrane with a MWCO of 300 kD in a batch-type operation analogous to the system shown in FIG. 3. The diafiltration occurred at a pH of 7–8, a temperature of 18–22° C., a feed solution inlet pressure of 10 psig, and a feed flow rate of about 25 ml/min. The extract/EDTA solution was diluted about 100-fold with a dilution solution comprising NaCl (50 mM) and EDTA (10 mM) in a total time of about 5 hours using 5 dilution cycles, each of which effected about a 2.5-fold dilution of the feed solution. The measured membrane flux rate was approximately 100 ml/hr. The permeate from the first cycle of the diafiltration was collected for Factor VII assessment. See Example 3C. The diafiltered extract retentate was subsequently dialyzed back to a solution comprising NaCl (50 mM) and Na₃Citrate (13 mM) using a simple 12,000 Dalton (12 kD) MWCO dialysis membrane.

The diafiltered extract was used to prepare a thromboplastin reagent by combining the diafiltered extract (25% by volume) with CaCl₂ (11 mM), HEPES, NaCl, PEG 8000, hexadimethrine bromide, mannitol, glycine, BSA and Pro-Clin™ 300. The thromboplastin reagent composition was evaluated in PT assays for a coagulation control Level I normal plasma, for a pooled-normal-plasma (PNP), for a coumarinized plasma (CP), and for a 99%⁺ Factor-VII-deficient plasma (F7D-I) using a CS-190 Optical Analyzer to determine PT clotting times. A control reagent prepared with untreated extract, but otherwise identical to the reagent composition being evaluated, was also evaluated. The results are shown in Table 3B.1

TABLE 3B.1

PT Clotting Times for Thromboplastin Reagent (25% Diafiltered Extract/300 MWCO/EDTA/10 psig)

| | Control Level I | PNP | Coumarin Plasma | F7D-I | CP/PNP |
| --- | --- | --- | --- | --- | --- |
| Untreated Extract (control) | 10.2 | 10.2 | 19.9 | 23.4 | 1.95 |
| Diafiltered Extract | 11.1 | 11.2 | 24.2 | 31.0 | 2.18 |

These data demonstrate a substantial increase in the sensitivity of the thromboplastin reagent comprising the difiltered extract as compared to the control reagent comprising untreated extract, with only a moderate increase in PT normal times.

In a second bench-scale experiment, another extract/EDTA solution prepared from a different thromboplastin extract in the same manner as described above was diafiltered through the same bench scale Pellicon XL™ cassette employed above after cleaning of the same, but with a feed solution inlet pressure of 20 psig, and a feed flow rate of about 45 ml/min. The extract/EDTA solution was diluted about 100-fold with a dilution solution comprising NaCl (50 mM) and EDTA (10 mM) in a total time of about 3 hours using 3 dilution cycles, each of which effected about a 5-fold dilution of the feed solution. The measured membrane flux rate was approximately 200 ml/hr. The diafiltered extract retentate was subsequently dialyzed back to a solution comprising NaCl (50 mM) and Na$_3$Citrate (11 mM) as described above.

The diafiltered extract was used to prepare two different thromboplastin reagent compositions. A first reagent composition was prepared by combining the diafiltered extract (25% by volume) with CaCl$_2$ (11 mM). A second reagent was prepared by combining the diafiltered extract (37.5% by volume) with CaCl$_2$ (11 mM). HEPES, NaCl, PEG 8000, hexadimethrine bromide, mannitol, glycine, BSA and Pro-Clin™ 300 were added to each of the reagent compositions.

The first thromboplastin reagent composition was evaluated in PT assays for a coagulation control Level I normal plasma, for a pooled-normal-plasma (PNP), and for a coumarinized plasma (CP) using a CS-190 Optical Analyzer to determine PT clotting times for the various plasma samples. A control assay employing a thromboplastin reagent prepared with untreated extract, but otherwise identical to the subject reagent composition, was also evaluated. The results are shown in Table 3B.2.

TABLE 3B.2

PT Clotting Times for Thromboplastin Reagent
(25% Diafiltered Extract/300 MWCO/EDTA/20 psig)

|  | Control Level 1 | PNP | Coumarin Plasma | CP/PNP |
|---|---|---|---|---|
| Untreated extract (25% extract) | 10.1 | 10.1 | 19.6 | 1.94 |
| Diafiltered extract (25% extract) | 10.5 | 10.7 | 23.1 | 2.16 |

The reagent composition comprising the diafiltered extract again demonstrated an increase in sensitivity and little effect on the normal times as compared to the control reagent.

The second thromboplastin reagent composition was evaluated in PT assays for a coagulation control Level I normal plasma, for a pooled-normal-plasma (PNP), for a coumarinized plasma (CP), for a 50% PNP, and for a 99%$^+$ Factor-VII-deficient plasma (F7D-I). PT clotting times were determined for the various plasma samples using both a CS-190 Optical Analyzer, and for comparison, using a mechanical PT test. The results for the optical analyzer are shown in Table 3B.3.

TABLE 3B.3

PT Clotting Times for Thromboplastin Reagent
(37.5% Diafiltered Extract/300 MWCO/EDTA/20 psig)

|  | Control Level 1 | PNP | Coumarin Plasma | F7D-1 | 50% PNP | CP/ PNP | Delta 100:50 PNP |
|---|---|---|---|---|---|---|---|
| CS-190 Optical PT clotting times (s) | 12.1 | 12.1 | 42.0 | 40.5 | 16.1 | 3.47 | 4.0 |

Example 3C: Contaminating Plasma Clotting Factors and Other Proteins are Removed from Diafiltered Extract Several experiments were performed that demonstrate removal of contaminating plasma clotting factors and other contaminating proteins from the thromboplastin solution by membrane permeation.

In a first experiment, the permeate from the first cycle of the diafiltration of the first bench-scale experiment of Example 3B (300 MWCO/EDTA/10 psig) was assessed for the presence of Factor VII and, independently, for the presence of procoagulant activity. The permeate collected from diafiltration was concentrated and dialyzed into a NaCl (50 mM)/Na$_3$Citrate (11 mM) solution to remove the EDTA. The permeate was then added to a Factor VII deficient plasma sample and evaluated with a PT assay employing a commercially-available thromboplastin reagent, ThromboMAX (Sigma Chemical, St. Louis Mo.). The assay results, reported in Table 3C.1(a), show that Factor VII was present in the permeate solution, since the PT assay times for the permeate sample were shorter for those for a 99$^+$% Factor VII-deficient plasma sample. Hence, these results demonstrate that active Factor VII was effectively separated from the thromboplastin extract solution by diafiltration. Moreover, as shown in Table 3C.1(b), the concentrated permeate had no demonstrable procoagulant activity, as evidenced by addition of the concentrated permeate to a coagulation control Level I plasma and measurement of clotting times, with Sigma Diagnostics ThromboMAX™ being used as a control. The PT assay initiated with the concentrated permeate was stopped after 200 seconds, with no clot detection.

TABLE 3C.1

Evaluation of Permeate for Factor VII

Table 3C.1(a)

|  | PT (s) |
|---|---|
| Coag Control Level I | 11.8 |
| Factor VII deficient plasma F7D-I | 32.7 |
| F7D-I plus 10 μl Example 1 solution | 32.9 |
| F7D-I plus 10 μl concentrated permeate | 30.6 |

Table 3C.1(b)

|  | Coag I PT (s) |
|---|---|
| Initiated with ThromboMAX | 12.1 |
| Initiated with conc permeate + CaCl$_2$ | >200.0 |

Figure 5:
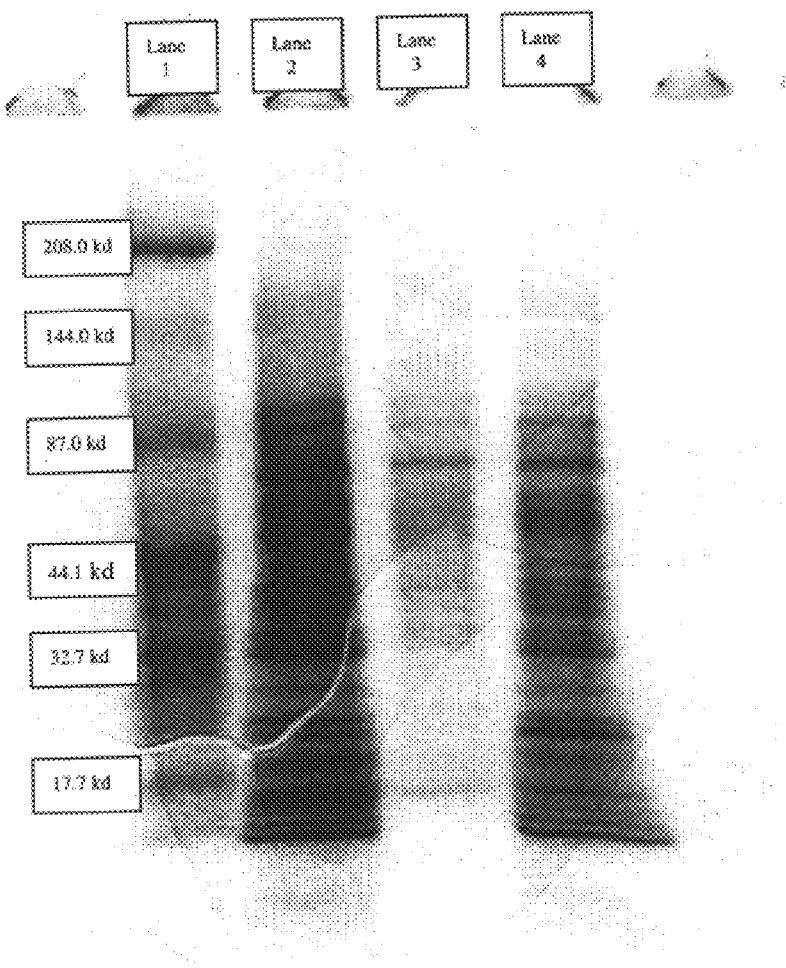
FIG. 5 is a photograph of a SDS-PAGE electrophoretic gel showing molecular weight standards (Lane 1) and the molecular weight distributions of proteins in: the solution phase of a thromboplastin extract prior to diafiltration (Lane 2); the retentate solution of the thromboplastin extract following diafiltration (Lane 3); and the permeate solution resulting from the diafiltration (Lane 4).

In a second experiment, a thromboplastin extract was prepared as in Example 2, and diafiltered using protocols analogous to those of Example 3B (300 MWCO/EDTA). The diafiltered extract was, along with an untreated control extract, cleared of solid particulates (and of Tissue Factor absorbed thereto) by centrifugation. The cleared supernatants of the diafiltered thromboplastin extract and of the untreated control extract, as well as the permeate resulting from the diafiltration, were electrophoretically evaluated by SDS-PAGE. The results, shown in FIG. 5, demonstrate that proteins present in untreated extract (Lane 2) were substantially separated by membrane permeation, with little of the proteins being retained in the treated extract retentate (Lane 3) and the majority of proteins passing through the membrane to the permeate (Lane 4).

Example 3D: Dialysis of BaSO$_4$/EDTA Thromboplastin Extract (300 kD MWCO)

A thromboplastin extract was prepared from rabbit-brain acetone powder (25 g) with an extraction solution (500 ml) comprising NaCl (50 mM), EDTA (10 mM) and BaSO$_4$ (5 g).

The EDTA/BaSO$_4$ extract was dialyzed—both with and without a small amount of CHAPS detergent—in 300 kD MWCO DispoDialyzers™ against a carrier solution comprising 50 mM NaCl and 10 mM EDTA. The dialyzed extract was subsequently dialyzed back into a NaCl (50 mM)/Na₃Citrate (11 mM) solution.

Each of the untreated extract, the extract dialyzed with CHAPS, and the extract dialyzed without CHAPS were analyzed in a thromboplastin reagent composition comprising the extract (35% by volume) and $CaCl_2$ (11 mM). HEPES, NaCl, PEG 8000, hexadimethrine bromide, mannitol, glycine, BSA and ProClin™ 300 were also added to the reagent composition. The thromboplastin reagent compositions were then evaluated in PT assays for a "Control Level I" normal plasma, for a pooled-normal-plasma (PNP), for a 80%-coumarinized plasma, for a 99%+ Factor-VII-deficient plasma and for International Sensitivity Index (ISI) using a CS-190 Optical Analyzer to determine PT clotting times. Two control assays were also evaluated—one using a thromboplastin reagent prepared with untreated extract, but otherwise identical to the subject reagent composition, and the other using a thromboplastin reagent prepared with an untreated extract dialyzed against a 12,000 Dalton (12 kD) MWCO membrane, but otherwise identical to the subject reagent composition. The results are shown in Table 3D.1

TABLE 3D.1

PT Clotting Times for Thromboplastin Reagent
(35% Dialyzed EDTA/BaSO₄ Extract/300 MWCO)

|  | Control Level I | PNP | Coumarin Plasma | F7D-I | Simple ISI |
|---|---|---|---|---|---|
| Untreated EDTA/BaSO₄ extract control | 10.7 | 11.1 | 23.6 | 26.7 | 1.79 |
| Dialyzed EDTA/BaSO₄ extract (12 kD) MWCO control | 10.5 | 10.7 | 25.4 | 27.1 | 1.56 |
| Dialyzed EDTA/BaSO₄ extract (300 kD MWCO w/out CHAPS) | 12.4 | 12.5 | 33.4 | 47.8 | 1.37 |
| Dialyzed EDTA/BaSO₄ extract (300 kD MWCO w/CHAPS) | 13.4 | 13.8 | 35.0 | 45.2 | 1.45 |

These data demonstrated a marked increase in the sensitivity of the dialyzed thromboplastin reagents relative to the control reagents, as evidenced by the decrease in the ISI value along with the large increase in the dynamic ranges for the clotting times of Factor VII-deficient plasma and for the coumarin-treated plasma. The presence of CHAPS during dialysis resulted in a detectable loss of procoagulant activity, as evidenced by the relatively longer normal times compared to reagents prepared from extracts dialyzed without CHAPS.

Example 3E: Dialysis of Frozen/Thawed Thromboplastin Extract (300 kD MWCO/EDTA)

A thromboplastin extract prepared as in Example 2 was frozen. The frozen extract was subsequently thawed, and made 10 mM in EDTA. The extract was dialyzed in 300 kD MWCO DispoDialyzers™ against a carrier solution comprising 50 mM NaCl and 10 mM EDTA, and was subsequently dialyzed back into a NaCl (50 mM)/Na₃Citrate (11 mM) solution.

The untreated extract and the dialyzed extract were analyzed in a thromboplastin reagent composition comprising the extract (35% by volume) and $CaCl_2$ (11 mM). HEPES, NaCl, PEG 8000, hexadimethrine bromide, mannitol, glycine, BSA and ProClin™ 300 were also added to the reagent composition. The thromboplastin reagent compositions were evaluated in PT assays for a "Control Level I" normal plasma, for a pooled-normal-plasma (PNP), for a 80%-coumarinized plasma, for a 99%+ Factor-VII-deficient plasma and for International Sensitivity Index (ISI) using a CS-190 Optical Analyzer to determine PT clotting times. A thromboplastin reagent prepared with untreated extract, but otherwise identical to the subject reagent composition, was employed as a control. The results are shown in Table 3E.1

TABLE 3E.1

PT Clotting Times for Thromboplastin Reagent
(35% Dialyzed Thawed Extract/300 MWCO/EDTA)

|  | Control Level 1 | PNP | Coumarin Plasma | F7D-I | Simple ISI |
|---|---|---|---|---|---|
| Untreated extract | 10.9 | 10.9 | 25.3 | 28.3 | 1.61 |
| Dialyzed EDTA to J6619, 300K MWCO | 12.5 | 12.6 | 35.1 | 50.8 | 1.32 |

Consistent with other results, these data demonstrate a marked improvement in the sensitivity of the reagent composition and an improvement in the Factor VII-deficient clotting times.

Example 4: Preparation of Thromboplastin Reagent

A thromboplastin reagent was prepared from a thromboplastin extract prepared as in Example 3B and comprised the extract (35% by volume), $CaCl_2$ (11 mM), HEPES (10 mM), NaCl (80 mM), PEG 8000 (0.75%), Na₃Citrate (3.5 mM), hexadimethrine bromide (12.5 mg/l), mannitol (2%), glycine (4%) and BSA (1%). The thromboplastin reagent was evaluated in PT assays for a coagulation control Level I normal plasma, for a pooled-normal-plasma (PNP), for a coumarinized plasma, and for a 99%+ Factor-VII-deficient plasma using a CS-190 Mechanical Analyzer to determine PT clotting times. The thromboplastin reagent prepared with untreated extract, but otherwise identical to the subject reagent composition, was employed as a control. The results are shown in Table 4.1

TABLE 4.1

PT Clotting Times for Thromboplastin Reagent
(35% Diafiltered Extract/300 MWCO—Pilot)

|  | PT (s) |
|---|---|
| PNP clotting time | 12.9 sec |
| Coumadin Plasma clotting time | 53.7 sec |
| FVII deficient plasma clotting time | 93.3 sec |
| Calculated simple ISI | 0.93 |

Example 5: Enzymatic digestion of contaminants in Thromboplastin Extracts

Human and bovine tissue factors have been reported to be resistant to chymotrypsin digestion. A further experiment to determine if an extract of greater sensitivity could be prepared by enzymatic digestion of residual rabbit clotting factors was performed.

Aliquots of rabbit brain acetone powder (RBAP) extract were incubated overnight at room temperature with varying concentrations of added chymotrypsin, followed by dialysis. These preparations were then tested as 42% extract pre-lyophillization thromboplastin reagents:

TABLE 5.1

Effects of Chymotrypsin on PT clotting times

| Pre-lyophillization thromboplastin reagent, plus Chymotrypsin treatment | PNP | F7D-I | Simple ISI |
|---|---|---|---|
| A: Zero enzyme, non-dialized | 12.0 | 71.0 | 1.13 |
| B: Zero enzyme, dialized | 12.7 | 111.0 | 1.10 |
| E: 3 ug/ml enzyme, dialized | 12.7 | 305.0 | 1.02 |

Chymotrypsin treatment of thromboplastin reagent demonstrated that the chymotrypsin treatment does not effect the tissue factor activity of the extracts or the normal values for PT assays while simultaneously improving the sensitivity of the product.

Example 6: Increased reagent sensitivity by modulating free calcium binding agents The performance of thromboplastin reagents supplemented with calcium binding reagents $Na_3$Citrate, ADA (N-2-acetamidol-2-iminodiacetic acid) and Bicine (N,N-bis (2-hydroxyethyl)glycine)were evaluated to determine the effect of modulating the free $Ca^{++}$ in the reagent. As shown in the tables below, the use of the Ca++ modulating agents increases the sensitivity of the reagent while keeping the normal PNP times within the expected range.

TABLE 6.1

Effects of various concentration of $Na_3$Citrate with HEPES buffer on PT clotting times.

|  | PNP | CP | 50% PNP | Simple ISI | D100-50 |
|---|---|---|---|---|---|
| 42% Extract, no chelator | 11.7 | 29.9 | 15.3 | 1.38 | 3.6 |
| 42% Extract, 1 mM NaCit | 12.0 | 32.4 | 15.2 | 1.30 | 3.2 |
| 42% Extract, 2 mM NaCit | 12.1 | 34.3 | 15.4 | 1.24 | 3.3 |
| 42% Extract, 3 mM NaCit | 12.5 | 40.9 | 15.7 | 1.09 | 3.2 |
| 42% Extract, 3.6 mM NaCit | 12.8 | 44.2 | 15.9 | 1.04 | 3.1 |

TABLE 6.2

Results of Bicine and ADA on Thromboplastin solution.

|  | PNP | CP | Simple ISI |
|---|---|---|---|
| 1 mM Bicine | 11.7 | 28.5 | 1.52 |
| 2 mM Bicine | 12.0 | 33.7 | 1.31 |
| 4 mM Bicine | 12.1 | 33.0 | 1.34 |
| 6 mM Bicine | 11.8 | 27.9 | 1.57 |
| 8 mM Bicine | 11.9 | 28.8 | 1.53 |
| 1 mM ADA | 11.9 | 34.0 | 1.29 |
| 2 mM ADA | 12.0 | 33.5 | 1.31 |
| 4 mM ADA | 15.5 | 118.3 | 0.66 |
| 6 mM ADA | 31.3 | NR | NR |
| 8 mM ADA | NR | NR | NR |

Example 7: Characterization of effect of diafiltration of Thromboplastin Extracts In order to characterize the effect of diafiltration of thromboplastin extracts independent from a functional assay, plasma hemoglobin assays of RBAP extracts, diafiltrated and non-diafiltrated, were performed.

The procedure was performed using the Sigma Diagnostics Plasma Hemoglobin Kit No. 527. The results were as follows:

| Sample | Calc'd Hb (mg/dl) |
|---|---|
| 10 ul 30 mg/dl hu Hb std. | 30.00 |
| 5 ul 30 mg/dl hu Hb std. | 14.87 |
| 10 ul clear supernatant non-diafiltered extract | 2.05 |
| 10 ul clear supernatant diafiltered extract | −0.51 |

The non-diafiltered extract has a brown or red tint presumably from the contaminants, whereas the diafiltered extract is clear and colorless. The results from the assay indicate that the non-diafiltered extract had a calculated Hb of 2.05 mg/dl. The diafiltered extract had a calculated Hb of −0.51 mg/dl indicating levels at or below the detection limit, demonstrating the effectiveness of the diafiltration technique in removal of contaminants from the thromboplastin extracts.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A method for preparing a composition which contains tissue thromboplastin, the method comprising:

extracting mammalian tissue with an extraction solution to form an extract which contains thromboplastin and at least one other plasma clotting factor selected from the group consisting of Factor VII, Factor II, Factor X, Factor IX, Factor XI, Factor XII, Protein C, Protein S, and Protein Z, and separating the at least one other plasma clotting factor from the extract by membrane permeation, thereby forming a composition which contains purified biologically active thromboplastin, and recovering the purified biologically active thromboplastin composition.

2. The method of claim 1 wherein the tissue is homogenized tissue.

3. The method of claim 1 wherein the tissue is dehydrated tissue.

4. The method of claim 1 wherein the tissue has been converted to an acetone powder prior to extraction.

5. The method of claim 1 wherein the extraction solution comprises an aqueous solution.

6. The method of claim 1 wherein the extraction solution comprises an organic acid salt.

7. The method of claim 1 wherein extraction solution comprises a citrate salt.

8. The method of claim 1 wherein the extraction solution comprises sodium citrate.

9. The method of claim 1 wherein the tissue is extracted with an extraction solution having an essential absence of calcium ions.

10. The method of claim 1 wherein the plasma clotting factor is Factor VII.

11. The method of claim 1 wherein the extract which contains thromboplastin and at least one other plasma clotting factor further comprises a calcium ion chelating agent.

12. The method claim 1 wherein the extract which contains thromboplastin and at least one other plasma clotting factor further comprises ethylenediaminetetraacetic acid at a concentration of at least 10 mM.

13. A method for preparing a composition which contains tissue thromboplastin, the method comprising:

extracting mammalian tissue with an extraction solution to form an extract which contains thromboplastin and at least one other plasma clotting factor, and separating the at least one other plasma clotting factor from the extract by membrane permeation with a semipermeable membrane having a molecular weight cutoff ranging from about 100,000 Daltons to about 1,000,000 Daltons, thereby forming a composition which contains purified biologically active thromboplastin, and recovering the purified biologically active thromboplastin composition.

14. The method of claim 13 wherein said semipermeable membrane has a molecular weight cutoff ranging from about 100,000 Daltons to about 500,000 Daltons.

15. The method of claim 13 wherein said semipermeable membrane has a molecular weight cutoff ranging from about 200,000 Daltons to about 400,000 Daltons.

16. The method of claim 13 wherein said semipermeable membrane has a molecular weight cutoff of about 300,000 Daltons.

17. The method of any one of claims 13–16 wherein the other plasma clotting factor is selected from the group consisting of Factor VII, Factor II, Factor X, Factor IX, Factor XI, Factor XII, Protein C, Protein S, and Protein Z.

18. The method of any one of claims 13–16 wherein said extract which contains thromboplastin and at least one other plasma clotting factor is contacted with a proteolytic enzyme prior to said separating by membrane permeation.

19. The method of any one of claims 13–16 wherein the other plasma clotting factor is selected from the group consisting of Factor VII, Factor II, Factor X, Factor IX, Factor XI, Factor XII, Protein C, Protein S, and Protein Z and wherein said extract which contains thromboplastin and at least/one other plasma clotting factor is contacted with a proteolytic enzyme prior to said separating by membrane permeation.

20. The method of any one of claims 13–16 wherein the extract which contains thromboplastin and at least one other plasma clotting factor further comprises a calcium ion chelating agent selected from the group consisting of ethylenediaminetetraacetic acid or any salt thereof, citrate, citrate salt, and ethylenebis(oxyethylenenitrilo)tetraacetic acid or any salt thereof.

21. The method of claim 20 wherein the extract which contains thromboplastin and at least one other plasma clotting factor further comprises dissociation agents selected from the group consisting of detergents, chaotropic agents, and buffers.

22. The method of any one of claims 1 or 13–16 wherein the extract which contains thromboplastin and at least one other plasma clotting factor further comprises dissociation agents selected from the group consisting of detergents, chaotropic agents, and buffers.

23. The method of any one of claims 13–16 wherein (i) the other plasma clotting factor is selected from the group consisting of Factor VII, Factor II, Factor X, Factor IX, Factor XI, Factor XII, Protein C, Protein S, and Protein Z, (ii) the extract which contains thromboplastin and at least one other plasma clotting factor further comprises a calcium ion chelating agent selected from the group consisting of ethylenediaminetetraacetic acid or any salt thereof, citrate, citrate salt, and ethylenebis(oxyethylenenitrilo)tetraacetic acid or any salt thereof, and (iii) said extract which contains thromboplastin and at least one other plasma clotting factor is contacted with a proteolytic enzyme prior to said separating by membrane permeation.

24. A method for preparing a composition which contains tissue thromboplastin, the method comprising:

extracting mammalian tissue with an extraction solution to form an extract which contains thromboplastin and at least one other plasma clotting factor, and contacting said extract with a proteolytic enzyme, and separating the at least one other plasma clotting factor from the extract by membrane permeation, thereby forming a composition which contains purified biologically active thromboplastin, and recovering the purified biologically active thromboplastin composition.

25. The method of claim 24 wherein said proteolytic enzyme is chymotrypsin.

* * * * *

UNITED STATES PATENT AND TRADEMARK OFFICE
CERTIFICATE OF CORRECTION

PATENT NO. : 6,391,609 B1
DATED : May 21, 2002
INVENTOR(S) : Marc D. Goldford

It is certified that error appears in the above-identified patent and that said Letters Patent is hereby corrected as shown below:

Column 25,
Line 11, "The method claim" should read -- The method of claim --.

Column 26,
Line 1, "at least/one" should read -- at least one --.
Line 4, "claims 13-16" should read -- claims 1 or 13-16 --.

Signed and Sealed this

Twentieth Day of January, 2004

JON W. DUDAS
*Acting Director of the United States Patent and Trademark Office*